United States Patent

Sebag et al.

Patent Number: 6,162,423
Date of Patent: Dec. 19, 2000

[54] WASHING AND CONDITIONING COMPOSITIONS CONTAINING SILICONE AND DIALKYL ETHER

[75] Inventors: Henri Sebag, Paris; Sandrine Decoster, Epinay sur Seine, both of France

[73] Assignee: L'Oreal S.A., Paris, France

[21] Appl. No.: 09/230,058

[22] PCT Filed: Jul. 21, 1997

[86] PCT No.: PCT/FR97/01350

§ 371 Date: Jan. 21, 1999

§ 102(e) Date: Jan. 21, 1999

[87] PCT Pub. No.: WO96/03155

PCT Pub. Date: Jan. 29, 1998

[30] Foreign Application Priority Data

Jul. 23, 1996 [FR] France ................................ 96 09252

[51] Int. Cl.⁷ .................................................. A61K 7/06
[52] U.S. Cl. .................. 424/70.12; 424/70.1; 424/70.19; 424/70.21; 424/70.27; 424/70.31; 514/63; 510/119; 510/122; 510/129; 510/130
[58] Field of Search .............................. 424/70.1, 70.12, 424/70.19, 70.21, 70.22, 70.27, 70.31; 510/119, 122, 129, 130; 514/63

[56] References Cited

U.S. PATENT DOCUMENTS

| | | |
|---|---|---|
| 2,261,002 | 10/1941 | Ritter . |
| 2,271,378 | 1/1942 | Searle . |
| 2,273,780 | 2/1942 | Dittmar . |
| 2,375,853 | 5/1945 | Kirby et al. . |
| 2,388,614 | 11/1945 | Kirby et al. . |
| 2,454,547 | 11/1948 | Bock et al. . |
| 2,961,347 | 11/1960 | Floyd . |
| 3,206,462 | 9/1965 | McCarty . |
| 3,227,615 | 1/1966 | Korden . |
| 3,589,578 | 6/1971 | Kamphausen . |
| 3,874,870 | 4/1975 | Green et al. . |
| 3,929,990 | 12/1975 | Green et al. . |
| 3,966,904 | 6/1976 | Green et al. . |
| 4,001,432 | 1/1977 | Green et al. . |
| 4,005,193 | 1/1977 | Green et al. . |
| 4,025,617 | 5/1977 | Green et al. . |
| 4,025,627 | 5/1977 | Green et al. . |
| 4,025,653 | 5/1977 | Green et al. . |
| 4,026,945 | 5/1977 | Green et al. . |
| 4,027,020 | 5/1977 | Green et al. . |
| 4,031,307 | 6/1977 | DeMartino et al. . |
| 4,131,576 | 12/1978 | Iovine et al. . |
| 4,693,935 | 9/1987 | Mazurek . |
| 4,728,571 | 3/1988 | Clemens et al. . |
| 4,919,923 | 4/1990 | Hoeffkes et al. . |
| 4,972,037 | 11/1990 | Garbe et al. . |
| 5,145,603 | 9/1992 | Paasch et al. . |
| 5,275,755 | 1/1994 | Sebag et al. ............... 252/174.15 |
| 5,655,200 | 8/1997 | Boettcher et al. ............... 252/307 |
| 5,789,372 | 8/1998 | Fabry et al. ............... 510/502 |

FOREIGN PATENT DOCUMENTS

| | | |
|---|---|---|
| 0 122 324 | 10/1984 | European Pat. Off. . |
| 0 181 773 | 5/1986 | European Pat. Off. . |
| 0 186 507 | 7/1986 | European Pat. Off. . |
| 0 264 844 | 4/1988 | European Pat. Off. . |
| 0 337 354 | 10/1989 | European Pat. Off. . |
| 0 342 834 | 11/1989 | European Pat. Off. . |
| 0 412 704 | 2/1991 | European Pat. Off. . |
| 0 412 707 | 2/1991 | European Pat. Off. . |
| 0 457 688 | 11/1991 | European Pat. Off. . |
| 0 582 152 | 2/1994 | European Pat. Off. . |
| 0 815 837 | 1/1998 | European Pat. Off. . |

(List continued on next page.)

OTHER PUBLICATIONS

Charles Todd et al., "Volatile Silicone Fluids for Cosmetic Formulations", Cosmetics and Toiletries, vol. 91, Jan. 1976, pp. 27–32.
Chemical Abstracts, vol. 79, No. 16, Oct. 22, 1973, Abstract No. 96851h.
M.R. Porter, "Handbook of Surfactants", Blacki & Son (Glasgow and London), 1991, pp. 116–178.
English language Derwent Abstract of DE 4 127 230.
English language Derwent Abstract of EP 0 457 688.
English language Derwent Abstract of FR 1 583 363.
English language Derwent Abstract of FR 2 077 143.
English language Derwent Abstract of FR 2 080 759.
English language Derwent Abstract of FR 2 134 451.
English language Derwent Abstract of FR 2 137 684.
English language Derwent Abstract of FR 2 162 025.
English language Derwent Abstract of FR 2 190 406.
English language Derwent Abstract of FR 2 252 840.
English language Derwent Abstract of FR 2 270 846.
English language Derwent Abstract of FR 2 280 361.
English language Derwent Abstract of FR 2 316 271.
English language Derwent Abstract of FR 2 320 330.
English language Derwent Abstract of FR 2 336 434.
English language Derwent Abstract of FR 2 368 508.
English language Derwent Abstract of FR 2 383 660.

(List continued on next page.)

Primary Examiner—Thurman K. Page
Assistant Examiner—Brian K. Seidleck
Attorney, Agent, or Firm—Finnegan, Henderson, Farabow, Garrett & Dunner L.L.P.

[57] ABSTRACT

Foaming compositions for washing and conditioning keratinous materials, particularly hair and/or skin, containing at least one silicone, at least one surfactant and at least one dialkylether that is solid at a temperature of about 30° C. and has formula (I):

$$R-O-R' \qquad (I)$$

the foaming power of said compositions greater than 50 ml, as well as washing and conditioning methods using said compositions, are disclosed; wherein in formula (I), each of R and R', which are the same or different, is a linear or branched, saturated or unsaturated alkyl radical containing 12–30 carbon atoms.

41 Claims, No Drawings

FOREIGN PATENT DOCUMENTS

| | | |
|---|---|---|
| 1 492 597 | 8/1967 | France . |
| 1 583 363 | 10/1969 | France . |
| 2 077 143 | 10/1971 | France . |
| 2080759 | 11/1971 | France . |
| 2 134 451 | 12/1972 | France . |
| 2 137 684 | 12/1972 | France . |
| 2 162 025 | 7/1973 | France . |
| 2 190 406 | 2/1974 | France . |
| 2 252 840 | 6/1975 | France . |
| 2 270 846 | 12/1975 | France . |
| 2 280 361 | 2/1976 | France . |
| 2 316 271 | 1/1977 | France . |
| 2 320 330 | 3/1977 | France . |
| 2 336 434 | 7/1977 | France . |
| 2 368 508 | 5/1978 | France . |
| 2 383 660 | 10/1978 | France . |
| 2 393 573 | 1/1979 | France . |
| 2 413 907 | 8/1979 | France . |
| 2 470 596 | 6/1981 | France . |
| 2 505 348 | 11/1982 | France . |
| 2 519 863 | 7/1983 | France . |
| 2 542 997 | 9/1984 | France . |
| 2 589 476 | 5/1987 | France . |
| 2 598 611 | 11/1987 | France . |
| 2 641 185 | 7/1990 | France . |
| 4 127 230 | 2/1993 | Germany . |
| 4 411 557 | 10/1995 | Germany . |
| 4 438 581 | 6/1996 | Germany . |
| 1 359 765 | 7/1974 | United Kingdom . |
| 2 208 664 | 4/1989 | United Kingdom . |
| 93/23009 | 11/1993 | WIPO . |
| 93/23446 | 11/1993 | WIPO . |
| 94/16668 | 8/1994 | WIPO . |
| 94/16677 | 8/1994 | WIPO . |
| 94/21226 | 9/1994 | WIPO . |
| 94/21593 | 9/1994 | WIPO . |
| 95/00578 | 1/1995 | WIPO . |
| 95/10259 | 4/1995 | WIPO . |
| 97/47274 | 12/1997 | WIPO . |

OTHER PUBLICATIONS

English language Derwent Abstract of FR 2 393 573.
English language Derwent Abstract of FR 2 413 907.
English language Derwent Abstract of FR 2 470 596.
English language Derwent Abstract of FR 2 505 348.
English language Derwent Abstract of FR 2 519 863.
English language Derwent Abstract of FR 2 542 997.
English language Derwent Abstract of FR 2 589 476.
English language Derwent Abstract of FR 2 598 611.
English language Derwent Abstract of FR 2 641 185.
English language Derwent Abstract of DE 4 411 557.
English language Derwent Abstract of DE 4 438 581.
English language Derwent Abstract of EP 0 815 837.

WASHING AND CONDITIONING COMPOSITIONS CONTAINING SILICONE AND DIALKYL ETHER

This application is a 371 of PCT/FR97/01350, filed Jul. 21, 1997.

The present invention relates to foaming compositions for washing and conditioning keratin substances, in particular the hair and/or the skin, based on silicone, on surfactant and on a fatty dialkyl ether which is solid at a temperature of less than or equal to about 30° C., the foaming power of the composition being greater than 50 ml, as well as to washing and conditioning processes using these compositions.

Compositions for washing keratin substances, in particular shampoos, are well known in the state of the art. It has already been proposed in the past to use silicones (conditioners) in such compositions in order to give the treated substances, in particular the hair, good cosmetic properties such as softness, sheen and easy disentangling.

Given the insoluble nature of the silicones which can be used in washing and conditioning foaming compositions, it is desirable to keep the silicones in uniform dispersion in the medium without, however, causing the viscosity to fall or reducing the compositions' detergent or foaming properties. The silicones must also be conveyed onto the keratin substances treated in order to give these substances, once the silicones have been applied, properties of softness, sheen and disentangling.

Few means exist at the present time for effectively maintaining insoluble conditioning agents in suspension in shampoo compositions, since this is a difficult problem to solve; in this regard, it has already been proposed to use long-chain ester or ether derivatives (pearlescent agents) (EP-A-181,773 and EP-A-457,688) or polysaccharides such as xanthan gum (gelling agents). However, pearlescent agents have crystallization problems which entail a change (increase) in the viscosity of the compositions over time; gelling agents also have drawbacks, namely, on the one hand, that the foam of detergent compositions containing xanthan gum is difficult to develop (poor initiation of foaming), and that, on the other hand, the compositions do not have a smooth texture and flow in blobs, which users do not find particularly agreeable.

Patent application EP-A-264,844 describes oil-in-water emulsions containing a dialkyl ether to obtain non-foaming and non-detergent liquid emulsions.

The Applicant has discovered, and this forms the subject of the invention, that by using at least one fatty dialkyl ether, which is solid at a temperature of less than or equal to about 30° C., in washing foaming compositions based on insoluble silicones and on surfactants, it is possible to obtain compositions with very good homogeneity and improved stability, in particular of the viscosity, while at the same time maintaining a sufficient foaming power. The compositions have a very good pearlescent effect as well as a viscosity which is satisfactory for application to keratin substances. Lastly, the compositions have a texture which is not runny and melting, thereby allowing good distribution of the composition over the entire head of hair when it is applied.

The compositions thus prepared have good detergent and foaming properties.

When they are applied to the hair, in addition to their washing properties, these compositions have hair conditioning properties, i.e. treated hair is shiny, disentangles easily and feels soft.

When they are applied to the skin, these compositions give keratin substances, in particular the hair, great softness.

The subject of the invention is thus novel washing and conditioning foaming compositions based on silicone, on surfactant and on dialkyl ether described below, the foaming power of the composition being greater than 50 ml.

Another subject of the invention consists of the washing and conditioning process using such compositions.

The subject of the invention is also the use of a fatty dialkyl ether, which is solid at a temperature of less than or equal to about 30° C., as an agent for suspending a silicone in a washing and conditioning foaming composition containing surfactants in a cosmetically acceptable aqueous medium.

Other subjects of the invention will become apparent on reading the description and the examples which follow.

The foaming power of the composition is measured according to the modified Ross Miles method (NF T 73-404 and ISO696). The modifications of the method are as follows: The measurement is performed at a temperature of 22° C. with osmosed water. The concentration of the solution is 2 g/l. The height of the drop is 1 m. The amount of composition which is dropped is 200 ml. These 200 ml of composition fall into a test-tube 50 mm in diameter containing 50 ml of the test composition. The measurement is performed 5 minutes after the composition has stopped flowing.

The foaming compositions for washing and conditioning keratin substances, in particular the hair and the skin, in accordance with the invention comprise, in a cosmetically acceptable aqueous medium, at least one silicone, at least one surfactant with detergent properties and at least one dialkyl ether of formula (I):

$$R\text{---}O\text{---}R' \qquad (I)$$

in which:

R and R', which may be identical or different, denote a linear or branched, saturated or unsaturated alkyl radical containing from 12 to 30 carbon atoms and preferably from 14 to 24 carbon atoms, R and R' being chosen such that the compound of formula (I) is solid at a temperature of less than or equal to about 30° C., the foaming power of the composition being greater than 50 ml.

More particularly, R and R' are identical.

Preferably, R and R' denote a stearyl radical.

The dialkyl ethers which can be used according to the invention can be soluble or insoluble in the compositions, but are preferably insoluble.

These compounds can be prepared according to the process described in patent application DE 41 27 230.

A distearyl ether which can be used in the context of the present invention is sold in particular under the name Cutina KE 3178 by the company Henkel.

The silicones which can be used in accordance with the invention are, in particular, polyorganosiloxanes that are insoluble in the composition and can be in the form of oils, waxes, resins or gums.

The organopolysiloxanes are defined in greater detail in Walter Noll's "Chemistry and Technology of Silicones" (1968) Academic Press. They can be volatile or non-volatile.

If volatile, the silicones are more particularly chosen from those having a boiling point of between 60° C. and 260° C., and even more particularly from:

(i) cyclic silicones containing from 3 to 7 and preferably from 4 to 5 silicon atoms. These are, for example, octamethylcyclotetrasiloxane sold in particular under the name "Volatile Silicone 7207" by Union Carbide or "Silbione 70045 V 2" by Rhône-Poulenc, decamethyl-cyclopentasiloxane sold under the name "Volatile Silicone 7158" by Union Carbide, and "Silbione 70045 V 5" by Rhône-Poulenc, and mixtures thereof.

Mention may also be made of cyclocopolymers of the dimethylsiloxanes/methylalkylsiloxane type, such as "Volatile Silicone FZ 3109" sold by the company Union Carbide, with the chemical structure:

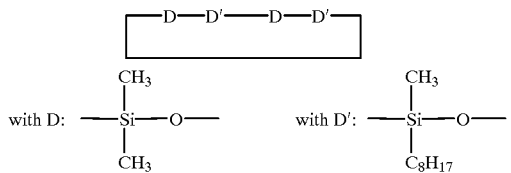

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones having 2 to 9 silicon atoms and having a viscosity of less than or equal to $5\times10^{-6}$ m$^2$/s at 25° C. An example is decamethyltetrasiloxane sold in particular under the name "SH 200" by the company Toray Silicone. Silicones belonging to this category are also described in the article published in Cosmetics and Toiletries, Vol. 91, Jan. 76, pp. 27–32, Todd & Byers "Volatile Silicone Fluids for Cosmetics".

Non-volatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups having a viscosity of from $5\times10^{-6}$ to 2.5 m$^2$/s at 25° C. and preferably $1\times10^{-5}$ to 1 m$^2$/s.

Among these polyalkylsiloxanes, mention may be made, in a non-limiting manner, of the following commercial products:

the Silbione oils of the series 47 and 70 047 or the Mirasil oils sold by Rhône-Poulenc, such as, for example, the oil 70 047 V 500 000;

the oils of the Mirasil series sold by the company Rhône-Poulenc;

the oils of the 200 series from the company Dow Corning;

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

In this category of polyalkylsiloxanes, mention may also be made of the products sold under the names "Abil Wax 9800 and 9801" by the company Goldschmidt, which are poly(C$_1$–C$_{20}$)alkylsiloxanes.

The polyalkylarylsiloxanes are chosen particularly from linear and/or branched polydimethylmethylphenylsiloxanes and polydimethyldiphenylsiloxanes with a viscosity of from $1\times10^{-5}$ to $5\times10^{-2}$ m$^2$/s at 25° C.

Among these polyalkylarylsiloxanes, mention may be made, by way of example, of the products sold under the following names:

the Silbione oils of the 70 641 series from Rhône-Poulenc;

the oils of the Rhodorsil 70 633 and 763 series from Rhône-Poulenc;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

The silicone gums which can be used in accordance with the invention are, in particular, polydiorganosiloxanes having high molecular masses of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:

polydimethylsiloxane
polydimethylsiloxanes/methylvinylsiloxane gums,
polydimethylsiloxane/diphenylmethylsiloxane,
polydimethylsiloxane/phenylmethylsiloxane,
polydimethylsiloxane/diphenylsiloxane/methylvinylsiloxane.

Products which can be used more particularly in accordance with the invention are mixtures such as:

mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a molecular weight of 500,000, dissolved in SF 1202 Silicone Fluid oil corresponding to decamethylcyclopentasiloxane;

mixtures of two PDMSs of different viscosities, and more particularly of a PDMS gum and a PDMS oil, such as the product SF 1236 from the company General Electric. The product SF 1236 is a mixture of a gum SE 30 defined above, having a viscosity of 20 m$^2$/s, and an oil SF 96, with a viscosity of $5\times10^{-6}$ m$^2$/s. This product preferably contains 15% SE 30 gum and 85% SF 96 oil.

The organopolysiloxane resins which can be used in accordance with the invention are crosslinked siloxane systems containing the following units: R$_2$SiO$_{2/2}$, R$_3$SiO$_{1/2}$, RSiO$_{3/2}$ and SiO$_{4/2}$ in which R represents a hydrocarbon-based group having from 1 to 16 carbon atoms or a phenyl group. Among these products, those particularly preferred are the ones in which R denotes a C$_1$–C$_4$ lower alkyl radical, more particularly methyl, or a phenyl radical.

Among these resins, mention may be made of the product sold under the name "Dow Corning 593" or those sold under the names "Silicone Fluid SS 4230 and SS 4267" by the company General Electric, which are silicones of dimethyl/trimethyl siloxane structure.

Mention may also be made of the trimethyl siloxysilicate resins sold in particular under the names X22-4914, X21-5034 and X21-5037 by the company Shin-Etsu.

The organomodified silicones which can be used in accordance with the invention are silicones as defined above and containing in their structure one or more organofunctional groups attached via a hydrocarbon-based radical.

Among the organomodified silicones, mention may be made of polyorganosiloxanes containing:

polyethylenoxy and/or polypropylenoxy groups optionally containing $C_6$–$C_{24}$ alkyl groups, such as the products known as dimethicone copolyol sold by the company Dow Corning under the name DC 1248 or the oils Silwet L 722, L 7500, L 77 and L 711 from the company Union Carbide and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$–$C_4$ aminoalkyl groups;

thiol groups such as the products sold under the names "GP 72 A" and "GP 71" from Genesee;

alkoxylated groups such as the product sold under the name "Silicone Copolymer F-755" by SWS Silicones and Abil Wax 2428, 2434 and 2440 by the company Goldschmidt;

hydroxyl groups such as the polyorganosiloxanes containing a hydroxyalkyl function, described in French patent application FR-A-85/16334 corresponding to formula (V):

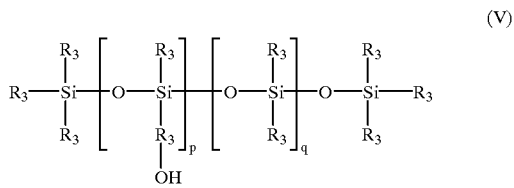

(V)

in which the radicals $R_3$, which may be identical or different, are chosen from methyl and phenyl radicals; at least 60 mol % of the radicals $R_3$ denoting methyl; the radical $R'_3$ is a divalent $C_2$–$C_{18}$ hydrocarbon-based alkylene chain unit; p is between 1 and 30 inclusive; q is between 1 and 150 inclusive;

acyloxyalkyl groups such as, for example, the polyorganosiloxanes described in French patent application FR-A-2 641 185 and corresponding to formula (VI):

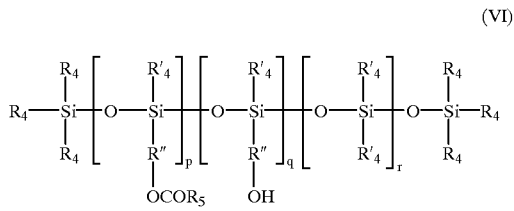

(VI)

in which:

$R_4$ denotes a methyl, phenyl, —$OCOR_5$ or hydroxyl group, only one of which radicals $R_4$ per silicon atom may be OH;

$R'_4$ denotes methyl, phenyl; at least 60 mol % of all of the radicals $R_4$ and $R'_4$ denoting methyl;

$R_5$ denotes $C_8$–$C_{20}$ alkyl or alkenyl;

R" denotes a linear or branched, divalent $C_2$–$C_{18}$ hydrocarbon-based alkylene radical;

r is between 1 and 120 inclusive;

p is between 1 and 30;

q is equal to 0 or is less than 0.5 p, p+q being between 1 and 30; the polyorganosiloxanes of formula (VI) can contain groups:

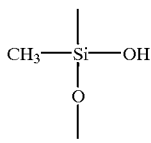

in proportions not exceeding 15% of the sum p+q+r.

The compounds of formula (VI) can be prepared of alkylcarboxylic type, such as those present in the product X-22-3701E from the company Shin-Etsu; 2-hydroxyalkyl sulphonate; 2-hydroxyalkyl thiosulphate such as the products sold by the company Goldschmidt under the names "Abil S201" and "Abil S255".

hydroxyacylamino groups, such as the polyorganosiloxanes described in patent application EP 342 834. Mention may be made, for example, of the product Q2-8413 from the company Dow Corning.

According to the invention, silicones can also be used comprising a polysiloxane portion and a portion consisting of a non-silicone organic chain, one of the two portions constituting the main chain of the polymer, the other being grafted onto the said main chain. These polymers are described, for example, in patent applications EP-A-412,704, EP-A-412,707, EP-A-640,105, WO 95/00578, EP-A-582,152 and WO 93/23009 and U.S. Pat. Nos. 4,693,935, 4,728,571 and 4,972,037. These polymers are preferably anionic or nonionic.

Such polymers are, for example, copolymers which can be obtained by radical polymerization starting with a monomer mixture consisting of:

a) 50 to 90% by weight of tert-butyl acrylate;

b) 0 to 40% by weight of acrylic acid;

c) 5 to 40% by weight of silicone macromer of formula:

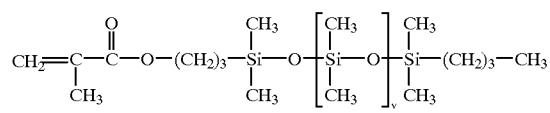

with v being a number ranging from 5 to 700; the weight percentages being calculated relative to the total weight of the monomers.

Other examples of grafted silicone polymers are, in particular, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl (meth) acrylate type.

According to the invention, all of the silicones can also be used in the form of emulsions.

The polyorganosiloxanes which are particularly preferred in accordance with the invention are:

nonvolatile silicones chosen from the family of polyalkylsiloxanes containing trimethylsilyl end groups, such as oils having a viscosity of between 0.2 and 2.5 m²/s at 25° C., such as the oils of the series DC200 from Dow Corning, in particular that with a viscosity of 60,000 cSt and 300,000 cSt, of the series Silbione 70047 and 47 and more particularly the oil 70 047 V 500,000, which are sold by the company Rhône-Poulenc, polyalkylsiloxanes containing dimethylsilanol end groups, such as dimethiconol, or polyalkylarylsiloxanes such as the oil Silbione 70641 V 200 sold by the company Rhône-Poulenc;

(i) Anionic Surfactant(s)

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Use may also be made of alkylpolyglycosides containing a sulphate, sulphonate, succinate or sulphosuccinate group, alkyl-D-galactosiduronic acids and their salts, and polyoxyalkylenated alkyl ether carboxylic acids and their salts, in particular those containing from 2 to 50 ethylene oxide groups, and mixtures thereof. Anionic surfactants such as polyoxyalkylenated carboxylic ether acids or salts are, in particular, those which correspond to formula (1) below:

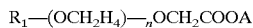

$$R_1-(OCH_2H_4)-_nOCH_2COOA \quad (1)$$

in which:
R$_1$ denotes an alkyl or alkylaryl group, and n is an integer or decimal (average value) which can range from 2 to 24 and preferably from 3 to 10, the alkyl radical having between 6 and 20 carbon atoms approximately, and aryl preferably denoting phenyl.

A denotes H, ammonium, Na, K, Li, Mg or a monoethanolamine or triethanolamine residue. Mixtures of compounds of formula (1) can also be used, in particular mixtures in which the groups R$_1$ are different.

Compounds of formula (1) are sold, for example, by the company Chem Y under the names Akypo (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, RO 50) or by the company Sandoz under the names Sandopan (DTC Acid, DTC).

(ii) Nonionic Surfactant(s)

Nonionic surfactants are likewise compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and ot propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, optionally oxyalkylenated (C$_8$–C$_{20}$)alkylpolyglycosides, N-alkylglucamine derivatives, amine oxides such as (C$_{10}$–C$_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s)

The amphoteric or zwitterionic surfactants, whose nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-soluble anionic group (for example carboxylate, sulphonate, sulphate, phosphate or phosphonate); mention may also be made of (C$_8$–C$_{20}$) alkylbetaines, sulphobetaines, (C$_8$–C$_{20}$) alkylamido(C$_1$–C$_6$)alkylbetaines or (C$_8$–C$_{20}$)alkylamido (C$_1$–C$_6$)alkylsulphobetaines.

Among the amine derivatives, mention may be made of the products sold under the name Miranol, as described in U.S. Pat. Nos. 2,528,378 and 2,781,354 and having the structures:

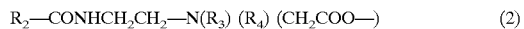

$$R_2-CONHCH_2CH_2-N(R_3)(R_4)(CH_2COO-) \quad (2)$$

in which: R$_2$ denotes an alkyl radical derived from an acid R$_2$—COOH present in hydrolysed coconut oil, a heptyl, nonyl or undecyl radical, R$_3$ denotes a β-hydroxyethyl group and R$_4$ denotes a carboxymethyl group; and

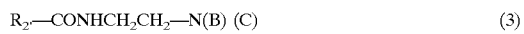

$$R_2-CONHCH_2CH_2-N(B)(C) \quad (3)$$

in which:
B represents —CH$_2$CH$_2$OX', C represents —(CH$_2$)$_z$—Y', with z=1 or 2,
X' denotes the —CH$_2$CH$_2$—COOH group or a hydrogen atom,
Y' denotes —COOH or the —CH$_2$—CHOH—SO$_3$H radical,
R$_2$ denotes an alkyl radical of an acid R$_9$—COOH present in coconut oil or in hydrolysed linseed oil, an alkyl radical, in particular a C$_7$, C$_9$, C$_{11}$ or C$_{13}$ alkyl radical, a C$_{17}$ alkyl radical and its iso form, or an unsaturated C$_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold under the trade name Miranol C2M concentrate by the company Rhône-Poulenc.

In the compositions in accordance with the invention, mixtures of surfactants are preferably used, and in particular mixtures of anionic surfactants with amphoteric, zwitterionic or nonionic surfactants. A particularly preferred mixture is a mixture consisting of at least one anionic surfactant with at least one amphoteric or zwitterionic surfactant.

The anionic surfactant used is preferably chosen from $(C_{12}-C_{14})$alkyl sulphates of sodium, of triethanolamine or of ammonium, the $(C_{12}-C_{14})$alkyl ether sulphates of sodium oxyethylenated with 2.2 mol of ethylene oxide, sodium cocoyl isethionate and sodium $(C_{14}-C_{16})$-α-olefin sulphonate, and mixtures thereof, with:

either an amphoteric surfactant such as the amine derivatives known as disodium cocoamphodipropionate or sodium cocoamphopropionate, sold in particular by the company Rhône-Poulenc under the trade name "Miranol C2M Conc." as an aqueous solution containing 38% active material, or under the name Miranol C32;

or zwitterionic surfactant, such as alkylbetaines, in particular the cocoylbetaine sold under the name "Dehyton AB 30" as an aqueous solution containing 32% AM by the company Henkel.

The dialkyl ether(s) corresponding to formula (I) used in accordance with the invention is (are) preferably present in proportions of between 0.1 and 10% relative to the total weight of the composition, and in particular between 0.5 and 5%.

The silicone(s) can be used in the compositions in accordance with the invention in proportions generally of between 0.05 and 20%, and preferably between 0.1 and 10%, by weight, relative to the total weight of the composition.

The surfactant(s) is (are) generally used in the compositions in accordance with the invention in sufficient proportions to give the composition a detergent nature, these proportions preferably being between 5 and 50% relative to the total weight of the composition, and in particular between 8 and 35%.

The pH of these compositions is generally between 3 and 9 are more particularly between 4 and 8.

The aqueous medium can consist solely of water or of a mixture of water and a cosmetically acceptable solvent such a $C_1-C_4$ lower alcohol, for instance ethanol, isopropanol, tert-butanol or n-butanol; alkylene glycolsrsuch as propylene glycol, and glycol ethers.

The compositions in accordance with the invention can contain, in addition to the combination defined above, viscosity modifiers such as electrolytes, or thickeners. Mention may be made in particular of sodium chloride, sodium xylenesulphonate, scleroglucans, xanthan gums, fatty acid alkanolamides, alkanolamides of carboxylic acid alkyl ether optionally oxyethylenated with up to 5 mol of ethylene oxide, such as the product sold under the name "Aminol A15" by the company Chem Y, crosslinked polyacrylic acids and crosslinked acrylic acid/$C_{10}-C_{30}$ alkyl acrylate copolymers. These viscosity modifiers are used in the compositions according to the invention in proportions which can range up to 10% by weight relative to the total weight of the composition.

The compositions in accordance with the invention can also contain up to 3% of pearlescent agents or opacifiers that are well known in the state of the art, such as, for example, sodium or magnesium palmitate, sodium or magnesium stearate or hydroxystearate, or acyl derivatives with a fatty chain, such as monostearates or distearates of ethylene glycol or of polyethylene glycol.

The compositions in accordance with the invention can also optionally contain other agents whose effect is to improve the cosmetic properties of the hair or the skin without, however, adversely affecting the stability of the compositions. Mention may be made in this respect of cationic surfactants, anionic or nonionic or cationic or amphoteric polymers, proteins, protein hydrolysates, ceramides, pseudoceramides, hydroxy acids, vitamins, panthenol and plant, animal, mineral or synthetic oils.

Among the cationic surfactants, mention may be made in particular (non-limiting list) of: optionally polyoxyalkylenated salts of primary, secondary or tertiary fatty amines; quaternary ammonium salts such as tetraalkylammonium, alkylamidoalkyltrialkylammonium, dialkyldihydroalkylammonium, trialkylbenzylammonium, trialkylhydroxyalkylammonium or alkylpyridinium chlorides or bromides; imidazoline derivatives, fatty diesters of dimethyltrihydroxyethylammonium; or amine oxides of cationic nature, the alkyl radicals having from 1 to 4 carbon atoms.

The conditioners of cationic polymer type which can be used in accordance with the present invention can be chosen from any of those known per se as improving the cosmetic properties of hair treated with detergent compositions, namely, in particular, those described in patent application EP-A-0,337,354 and in French patent applications FR-A-2, 270,846, 2,383,660, 2,598,611, 2,470,596 and 2,519,863.

Even more generally, for the purposes of the present invention, the expression "cationic polymer" denotes any polymer containing cationic groups and/or groups which can be ionized into cationic groups.

The preferred cationic polymers are chosen from those which contain units containing primary, secondary, tertiary and/or quaternary amine groups which can either form part of the main polymer chain or be attached to a side substituent that is directly attached to the main chain.

The cationic polymers used generally have a molecular mass of between 500 and $5 \times 10^6$ approximately and preferably between $10^3$ and $3 \times 10^6$ approximately.

Among the cationic polymers, mention may be made more particularly of quaternized proteins (or protein hydrolysates) and polymers of the polyamine, polyaminoamide and polyquaternary ammonium type. These are known products.

The quaternized proteins or protein hydrolysates are, in particular, chemically modified polypeptides bearing quaternary ammonium groups at the end of the chain or grafted thereto. Their molecular mass can range, for example, from 1500 to 10,000 and in particular from 2000 to 5000 approximately. Among these compounds, mention may be made in particular of:

collagen hydrolysates bearing triethylammonium groups, such as the products sold under the name "Quat-Pro E" by the company Maybrook and referred to in the CTFA dictionary as "Triethonium Hydrolyzed Collagen Ethosulfate";

collagen hydrolysates bearing trimethylammunium and trimethylstearylammonium chloride groups, sold under the name "Quat-Pro S" by the company Maybrook and referred to in the CTFA dictionary as "Steartrimonium Hydrolyzed Collagen";

animal protein hydrolysates bearing trimethylbenzylammonium groups such as the products sold under the name "Crotein BTA" by the company Croda and referred to in the CTFA dictionary as "Benzyltrimonium hydrolyzed animal protein";

protein hydrolysates bearing, on the polypeptide chain, quaternary ammonium groups containing at least one alkyl radical having from 1 to 18 carbon atoms.

Among these protein hydrolysates, mention may be made of, inter alia:

"Croquat L" in which the quaternary ammonium groups contain a $C_{12}$ alkyl group;

"Croquat M" in which the quaternary ammonium groups contain $C_{10}$–$C_{18}$ alkyl groups;

"Croquat S" in which the quaternary ammonium groups contain a $C_{18}$ alkyl group;

"Crotein Q" in which the quaternary ammonium groups contain at least one alkyl group having 1 to 18 carbon atoms.

These various products are sold by the company Croda.

Other quaternized proteins or hydrolysates are, for example, those corresponding to the formula:

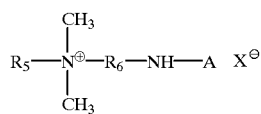

(II)

in which X is an anion of an organic or inorganic acid, A denotes a protein residue derived from collagen protein hydrolysates, $R_5$ denotes a lipophilic group containing up to 30 carbon atoms and $R_6$ represents an alkylene group having 1 to 6 carbon atoms. Mention may be made, for example, of the products sold by the company Inolex under the name "Lexein QX 3000", referred to in the CTFA dictionary as "Cocotrimonium Collagen Hydrolysate".

Mention may also be made of quaternized plant proteins such as wheat, corn or soybean proteins: as quaternized wheat proteins, mention may be made of those sold by the company Croda under the name "Hydrotriticum WQ or QM", referred to in the CTFA dictionary as "Cocodimonium Hydrolysed Wheat Protein", "Hydrotriticum QL", referred to in the CTFA dictionary as "Lauridimonium Hydrolysed Wheat Protein" or "Hydrotriticum QS", referred to in the CTFA dictionary as "Steardimonium Hydrolysed Wheat Protein".

The polymers of the polyquaternary ammonium, polyamidoamide and polyamine type which can be used in accordance with the present invention and which may be mentioned in particular are those described in French patents Nos. 2,505,348 and 2,542,997. Of these polymers, the following may be mentioned:

(1) Quaternized or non-quaternized vinylpyrrolidone/dialkylaminoalkyl acrylate or methacrylate copolymers, such as the products sold under the name "Gafquat" by the company ISP such as, for example, Gafquat 734, 755 or HS100 or alternatively the product known as "Copolymere 937". These polymers are described in detail in French patents 2,077,143 and 2,393,573.

(2) The cellulose ether derivatives containing quaternary ammonium groups, described in French patent 1,492,597, and in particular polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial pro-ducts corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361;

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polymaoamide; these polyamino amides can be alkylated or, if they contain one or more tertiary amine functions, they can be quaternized. Such polymers are described, in particular, in French patents 2,252,840 and 2,368,508;

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialylenetriamine polymers in which the alkyl radical contains from 1 to 4 carbon atoms and preferably denotes methyl, ethyl or propyl. Such polymers are described in particular in French patent 1,583,363.

Among these derivatives, mention may be made more particularly of the adipic acid/ dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of methyldiallylamine or of dimethyldiallylammonium, such as the homopolymers or copolymers containing, as main constituent of the chain, units corresponding to formula (VI) or (VI'):

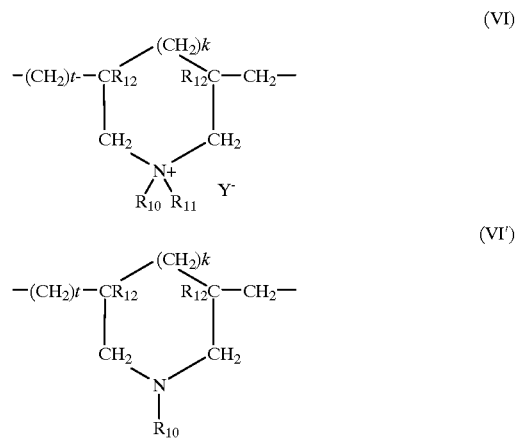

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, or a lower amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406.

Among the polymers defined above, mention may be made more particularly of the dimethyldiallylammonium chloride homopolymer sold under the name "Merquat 100" by the company Merck.

(10) The quaternary diammonium polymer containing repeating units corresponding to the formula:

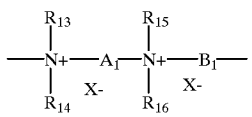

in which formula (VII):

$R_{13}$, $R_{14}$, $R_{15}$, and $R_6$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO—D—OC—$(CH_2)_n$— in which D denotes:

a) a glycol residue of formula: —O—Z—O—, where Z denotes a linear or branched hydrocarbon radical or a group corresponding to one of the following formulae:

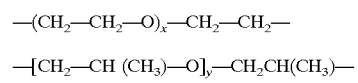

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical

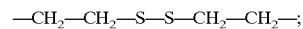

d) a ureylene group of formula: —NH—CO—NH—.

Preferably, $X^-$ is an anion such as chloride or bromide.

These polymers generally have a number-average molecular mass of between 1000 and 100,000.

Polymers of this type are described in particular in French patents 2,320,330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) Polyquaternary ammonium polymers consisting of units of formula (VIII):

(VIII)

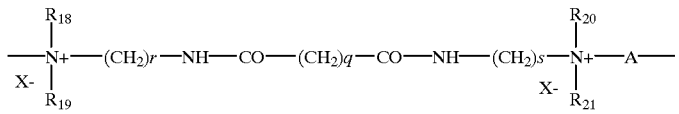

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer between 1 and 6, with the proviso that $R_{18}$, $R_{19}$, $R_{20}$ and $R_2$, do not simultaneously represent a hydrogen atom, r and s, which may be identical or different, are integers from 1 to 6, q is equal to 0 or to an integer from 1 to 34, X denotes a halogen atom, A denotes a dihalide radical or preferably represents —CH$_2$—CH$_2$—O—CH$_2$—CH$_2$—.

Such compounds are described in particular in patent application EP-A-122,324.

Among these products, mention may be made, for example, of "Mirapol A 15", "Mirapol AD1", "Mirapol AZ1" and "Mirapol 175" sold by the company Miranol.

(12) Homopolymers or copolymers derived from acrylic or methacrylic acids and containing units:

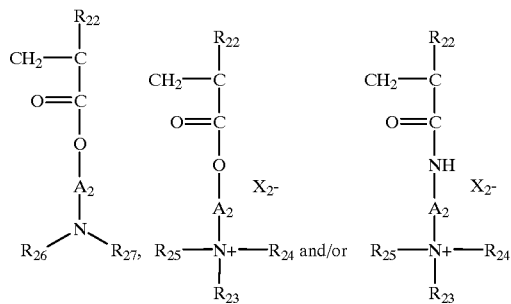

in which the groups $R_{22}$ independently denote H or CH$_3$, the groups $A_1$ independently denote a linear or branched alkyl group of 1 to 6 carbon atoms or a hydroxyalkyl group of 1 to 4 carbon atoms, the groups $R_{23}$, $R_{24}$ and $R_{25}$, which may be identical or different, independently denote an alkyl group of 1 to 18 carbon atoms or a benzyl radical, the groups $R_{26}$ and $R_{27}$ represent a hydrogen atom or an alkyl group of 1 to 6 carbon atoms, $X_2^-$ denotes an anion, for example methosulphate or halide, such as chloride or bromide.

The comonomer(s) which can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(13) Quaternary polymers of vinylpyrrolidone and of vinylimidazole, such as, for example, the products sold under the names Luviquat FC 905, FC 550 and FC 370 by the company BASF.

(14) Polyamines such as Polyquart H sold by Henkel, listed under the name "Polyethylene glycol (15) tallow polyamine" in the CTFA dictionary.

(15) Crosslinked methacryloyloxyethyltrimethylammonium chloride polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl ammonium chloride copolymer (20/80 by weight) in the form of a dispersion containing 50% by weight of the said copolymer in mineral oil can be used more particularly. This dispersion is sold under the name "Salcare SC 92" by the company Allied Colloids. A crosslinked methacryloyloxyethyltrimethylammonium chloride homopolymer containing about 50% by weight of the homopolymer in mineral oil can also be used. This dispersion is sold under the name "Salcare SC 95" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

According to the invention, polymers chosen from Mirapol, the compound of formula (VII) in which $R_{13}$, $R_{14}$, $R_{15}$ and $R_{16}$ represent a methyl radical, $A_1$ represents a radical of formula —(CH$_2$)$_3$— and $B_1$ represents a radical of formula —(CH$_2$)$_6$— and X$^-$ represents a chloride anion (referred to hereinbelow as Mexomer PC) and the compound of formula (VII) in which $R_{13}$ and $R_{14}$ represent an ethyl radical, $R_{15}$ and $R_{16}$ represent a methyl radical, $A_1$ and $B_1$ represent a radical of formula —(CH$_2$)$_3$— and X$^-$ represents a bromide anion (referred to hereinbelow as Mexomer PAK) can be used more particularly.

Among all the cationic polymers which can be used in the context of the present invention, it is preferred to use quaternary cellulose ether derivatives such as the products sold under the name "JR 400" by the company Union Carbide Corporation, cyclopolymers, in particular the dimethyldiallylammonium chloride homopolymers and the copolymers of dimethyldiallylammonium chloride and of acrylamide, sold under the names "Merquat 550" and "Merquat S" by the company Merck, cationic polysaccharides and more particularly guar gum modified with 2,3-epoxypropyltrimethylammonium chloride sold under the name "Jaguar C13S" by the company Meyhall.

By way of amphoteIric polymer, mention may be made of:

polymers preferably containing about 60 to about 99% of units derived from a, dialkyldiallylammonium monomer, in which the alkyl groups contain from 1 to 18 carbon atoms and preferably about 1 to about 40% of units derived from monomers chosen from acrylic and methacrylic acids.

The preferred polymers are polymers of diallyldimethyl- or of diallydiethylammonium and of acrylic acid, such as the product sold under the name Merquat 280 by the company Merck.

chitosans partially modified with $C_4$–$C_8$ dicarboxylic acids, such as those described in FR 2,137,684. The degree of modification can be between 30 and 90% by weight relative to the total weight of the chitosan. These chitosans can be totally deacetylated.

According to the invention, the cationic polymer(s) can represent from 0.001% to 10% by weight, preferably from 0.005% to 5% by weight and even more preferably from 0.01% to 3% by weight, of the total weight of the final composition.

The compositions according to the invention can also contain foam synergists such as $C_{10}$–$C_{18}$ 1,2-alkanediols or fatty alkanolamides derived from mono- or diethanolamine.

These compositions can also contain various adjuvants commonly used in cosmetics, such as fragrances, preserving agents, sequestering agents, foam stabilizers and acidifying or basifying agents that are well known in cosmetics.

The compositions according to the invention are preferably used as shampoos for washing and conditioning the hair, and, in this case, they are applied to wet hair in amounts which are efficient to wash it, this application being followed by rinsing with water, after optionally leaving the compositions on the hair for a period of time.

The compositions in accordance with the invention can also be used as shower gels for washing and conditioning the hair and the skin, in which case they are applied to wet skin and hair and are rinsed after application.

The examples which follow are intended to illustrate the invention:

EXAMPLE 1

A shampoo composition was prepared, containing:

| | |
|---|---|
| Sodium lauryl ether sulphate (70/30 C12/C14) containing 2.2 mol of ethylene oxide (AM = active material) | 14 gAM |
| Imidazoline-based amphoteric surfactant sold under the name Miranol C2M by the company Rhône-Poulenc at 40% AM | 4 gAM |
| Sodium cetostearyl sulphate (50/50 by weight) | 0.75 g |
| Guar gum modified with 2,3-epoxypropyltrimethylammonium chloride, sold under the name Jaguar C 13 S by the company Rhône-Poulenc | 0.2 g |
| Polydimethylsiloxane sold under the name Mirasil DM 500,000 par the company Rhône-Poulenc | 2.6 g |
| Distearyl ether | 4 g |
| Cetylstearyl alcohol | 1 g |
| Stearyl alcohol oxyethylenated with 10 mol of ethylene oxide (Brij 76 from ICI) | 0.8 g |
| Citric acid        qs | pH 5 |
| Fragrance, preserving agents        qs | |
| Demineralized water        qs | 100 g |

The composition is stable and has a good pearlescent effect.

Shampooing is carried out by applying about 12 g of the composition to premoistened hair. The shampoo is worked into a lather and is then rinsed out thoroughly with water.

The hair is easy to comb, is shiny and feels soft.

The foaming power of the composition is greater than 100 ml.

EXAMPLE 2

A shampoo composition was prepared, containing:

| | |
|---|---|
| Sodium lauryl ether sulphate (70/30 C12/C14) containing 2.2 mol of ethylene oxide (AM = active material) | 14 gAM |
| Cocoylbetaine as an aqueous solution containing 32% active material (Dehyton AB 30 from Henkel) | 2.56 gAM |
| Sodium cetostearyl sulphate (50/50 by weight) | 0.75 g |
| Polydimethylsiloxane of viscosity 60,000 cSt, sold by the company Dow Corning under the name Fluid DC 200 - 60,000 cSt | 1.5 g |
| Amodimethicone sold as a cationic emulsion containing 35% active material, under the name Fluid DC 939 by the company Dow Corning | 1 gMA |
| Distearyl ether | 1.5 g |
| Ethylene glycol distearate | 1 g |
| Coconut acid monoisopropanolamide | 2 g |
| Citric acid        qs | pH 5 |
| Fragrance, preserving agents        qs | |
| Demineralized water        qs | 100 g |

The composition is stable and has a good pearlescent effect.

Shampooing is carried out by applying about 12 g of the composition to premoistened hair. The shampoo is worked into a lather and is then rinsed out thoroughly with water.

The hair is easy to comb, is shiny and feels soft.

The foaming power of the composition is greater than 100 ml.

EXAMPLE 3

A shampoo composition was prepared, containing:

| | |
|---|---|
| Sodium lauryl ether sulphate (70/30 C12/C14) containing 2.2 mol of ethylene oxide (AM = active material) | 14 gAM |
| Imidazoline-based amphoteric surfactant sold under the name Miranol C2M by the company Rhône-Poulenc at 40% AM | 4 gAM |
| Sodium cetostearyl sulphate (50/50 by weight) | 0.75 g |
| Guar gum modified with 2,3-epoxypropyltrimethylammonium chloride, sold under the name Jaguar C 13 S by the company Rhône-Poulenc | 0.2 g |
| Polydimethylsiloxane of viscosity 60,000 cSt sold by the company Dow Corning under the name Fluid DC 200 - 60,000 cSt | 2.6 g |
| Distearyl ether | 2.5 g |
| Oxyethylenated mixture of decyl, lauryl and palmityl alchol (85/8.5/6.5 by weight), sold under the name Mergital BL 309 by the company Henkel | 1.5 g |
| Citric acid        qs | pH 5 |
| Fragrance, preserving agents        qs | |
| Demineralized water        qs | 100 g |

The composition is stable and has a good pearlescent effect.

Shampooing is carried out by applying about 12 g of the composition to premoistened hair. The shampoo is worked into a lather and is then rinsed out thoroughly with water.

The hair is easy to comb, is shiny and feels soft.
The foaming power of the composition is greater than 100 ml.

EXAMPLE 4

A shampoo composition was prepared, containing:

| | |
|---|---|
| Sodium lauryl ether sulphate (70/30 C12/C14) containing 2.2 mol of ethylene oxide (AM = active material) | 14 gAM |
| Cocoylbetaine as an aqueous solution containing 32% active material (Dehyton AB 30 from Henkel) | 2.56 gAM |
| Sodium cetostearyl sulphate (50/50 by weight) | 0.75 g |
| α,ω-Hydroxy polydimethylsiloxane as an aqueous emulsion containing 51% AM, sold by the company OSI under the name TP512 | 1.5 gAM |
| Distearyl ether | 2.5 g |
| Ethylene glycol distearate | 1 g |
| Coconut acid monoisopropanolamide | 2 g |
| Citric acid    qs | pH 5 |
| Fragrance, preserving agents    qs | |
| Demineralized water    qs | 100 g |

This composition has the same properties as those of the composition of Example 1.

We claim:

1. A foaming composition for washing and conditioning keratin substances, said foaming composition comprising, in a cosmetically acceptable aqueous medium, at least one silicone, at least one surfactant having detergent properties and at least one dialkyl ether which is solid at a temperature of less than or equal to about 30° C., of formula (I):

$$R\text{—}O\text{—}R' \quad (I)$$

in which:
R and R', which are identical or different, denote a linear or branched, saturated or unsaturated alkyl radical containing from 12 to 30 carbon atoms, wherein said foaming composition has a foaming power of greater than 50 ml.

2. A composition according to claim 1, wherein in said formula (I), R and R' are identical.

3. A composition according to claim 2, wherein R and R' are each a stearyl radical.

4. A composition according to claim 1, wherein said at least one silicone is a polyorganosiloxane that is insoluble in the composition and is in the form of an oil, a wax, a resin or a gum.

5. A composition according to claim 4, wherein said polyorganosiloxane is a non-volatile polyorganosiloxane and is a polyalkylsiloxane, a polyarylsiloxane, a polyalkylarylsiloxane, a silicone gum, a resin, a polyorganosiloxane modified with an organofunctional group, or a mixture thereof.

6. A composition according to claim 5, wherein:
(a) said polyalkylsiloxane is:
a polydimethylsiloxane containing a trimethylsilyl end group;
a polydimethylsiloxane containing a dimethylsilanol end group; or
a poly($C_1$—$C_{20}$)alkylsiloxane;
(b) said polyalkylarylsiloxane is:
a linear and/or branched polydimethylmethylphenylsiloxane or a polydimethyldiphenylsiloxane with a viscosity ranging from $1\times10^{-5}$ to $5\times10^{-2}$ m$^2$/s at 25° C.;

(c) said silicone gum is a polydiorganosiloxane with a molecular mass ranging from 200,000 to 1,000,000, said polydiorganosiloxane being alone or in the form of a mixture in a solvent;
(d) said resin is a resin containing units:
$R_3SiO_{1/2}$, $R_2SiO_{2/2}$, $RSiO_{3/2}$, and $SiO_{4/2}$ in which R represents a hydrocarbon-based group containing from 1 to 16 carbon atoms or a phenyl group;
(e) said organomodifed silicone contains in its structure one or more organofunctional groups attached via a hydrocarbon-based radical.

7. A composition according to claim 6, wherein the silicone gum used, alone or in the form of a mixture, is:
a polydimethylsiloxane
a polydimethylsiloxane/methylvinylsiloxane,
a polydimethylsiloxane/diphenylsiloxane,
a polydimethylsiloxane/phenylmethylsiloxane,
a polydimethylsiloxane/diphenylsiloxane/methylvinylsiloxane,
a mixture formed from a polydimethylsiloxane hydroxylated at the end of the chain and from a cyclic polydimethylsiloxane,
a mixture formed from a polydimethylsiloxane gum and from a cyclic silicone, or
a mixture of polydimethylsiloxanes of different viscosities.

8. A composition according to claim 6, wherein the organomodified silicone is a polyorganosiloxane containing:
a) a polyethylenoxy and/or polypropylenoxy group;
b) a substituted or unsubstituted amine group;
c) a thiol group;
d) an alkoxylated group;
e) a hydroxyalkyl group of the following formula:

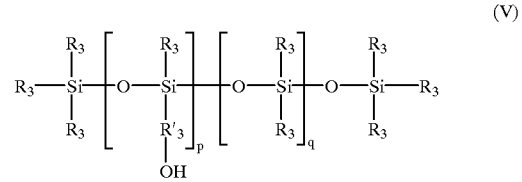

(V)

in which
the radicals $R_3$, which are identical or different, are a methyl or a phenyl radical, at least 60 mol % of the radicals $R_3$ being methyl;
the radical $R'_3$ is a divalent $C_2$–$C_{18}$ hydrocarbon-based alkylene chain unit;
p ranges from 1 to 30 inclusive; and
q ranges from 1 to 150 inclusive;
f) an acyloxyalkyl group of the following formula:

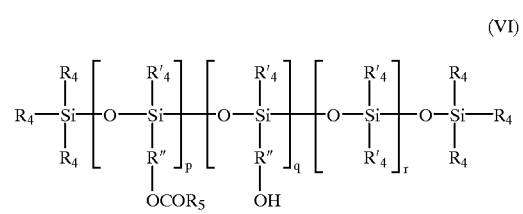

(VI)

in which:
$R_4$ is methyl, phenyl, —OCOR$_5$ or hydroxyl, where at most one radical $R_4$ per silicon atom may be OH;

R'$_4$ is methyl, phenyl, wherein at least 60 mol % of all of the radicals R$_4$ and R'$_4$are methyl;

R$_5$ is a C$_8$–C$_{20}$ alkyl or alkenyl;

R" is a linear or branched, divalent C$_2$–C$_{18}$ hydrocarbon-based alkylene radical;

r ranges from 1 to 120 inclusive;

p ranges from 1 to 30;

q is equal to 0 or is less than 0.5 p, where p+q ranges from 1 to 30; and the polyorganosiloxane of formula (VI) can contain at least one group:

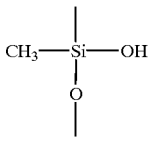

in a proportion not exceeding 15% of the sum p+q+r;

g) an alkylcarboxylic group;

h) a 2-hydroxyalkyl sulphonate group;

i) a 2-hydroxyalkyl thiosulphonate group; or j) a hydroxyacylamino group.

9. A composition according to claim 4, wherein the polyorganosiloxane is a polyalkylsiloxane containing a trimethylsilyl end group, a polyalkylsiloxane containing a dimethylsilanol end group, a polyalkylarylsiloxane, a polyorganosiloxane resin, a mixture of two polydimethylsiloxanes comprising a gum and an oil of different viscosities, or a mixture of organosiloxanes and of cyclic silicones.

10. A composition according to claim 1, wherein said at least one silicone is a volatile silicone.

11. A composition according to claim 10, wherein the volatile silicone is:

a cyclic silicone containing from 3 to 7 silicon atoms;

a dimethylsiloxane/methylalkylsiloxane cyclopolymer having the structure:

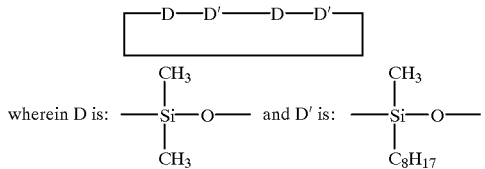

a mixture of cyclic silicones with organosilicon compounds; and a linear volatile silicone containing from 2 to 9 silicon atoms and having a viscosity of less than or equal to 5×10$^{-6}$ m$^2$/s at 25° C.

12. A composition according to claim 1, wherein said at least one surfactant having detergent properties is an anionic, amphoteric, zwitterionic, or nonionic surfactant, or a mixture thereof.

13. A composition according to claim 12, wherein said mixture of surfactants is a mixture of anionic surfactants with amphoteric, zwitterionic, or nonionic surfactants.

14. A composition according to claim 1, wherein said at least one silicone is present in an amount ranging from 0.05 to 20% by weight, relative to the total weight of the composition.

15. A composition according to claim 14, wherein said at least one silicone is present in an amount ranging from 0.1 and 10% by weight relative to the total weight of the composition.

16. A composition according to claim 1, wherein said at least one dialkyl ether of formula (I) is present in an amount ranging from 0.1 to 10% by weight relative to the total weight of the composition.

17. A composition according to claim 16, wherein said at least one dialkyl ether is present in an amount ranging from 0.5 to 5% by weight relative to the total weight of the composition.

18. A composition according to claim 1, wherein said at least one surfactant is present in a sufficient amount to give the composition a detergent nature.

19. A composition according to claim 1, wherein said at least one surfactant is present in an amount ranging from 5 to 50% by weight relative to the total weight of the composition.

20. A composition according to claim 19, wherein said at least one surfactant is present in an amount ranging from 8 to 35% by weight relative to the total weight of the composition.

21. A composition according to claim 1, wherein said composition has a pH ranging from 3 to 9.

22. A composition according to claim 21, wherein said pH ranges from 3 to 8.

23. A composition according to claim 1, wherein said aqueous medium comprises water or of a mixture of water and a cosmetically acceptable solvent selected from a lower alcohol, an alkylene glycol and a glycol ether.

24. A composition according to claim 1, further comprising a viscosity modifier or a thickener present in an amount ranging up to 10% by weight relative to the total weight of the composition.

25. A composition according to claim 24, wherein said viscosity modifier is an electrolyte.

26. A composition according to claim 1, further comprising up to 3% of a pearlescent agent and/or an opacifier.

27. A composition according to claim 1, further comprising at least one adjuvant to improve the cosmetic properties of said composition, said at least one adjuvant being a cationic surfactant, an anionic, nonionic, cationic, or amphoteric polymer, or an optionally quaternized protein.

28. A composition according to claim 27, wherein said cationic polymer is a polymer containing a primary, secondary, tertiary, or quaternary amine group forming part of the polymer chain or directly connected thereto and having a molecular weight from about 500 to about 5,000,000.

29. A composition according to claim 28, wherein said cationic polymer is a quaternary cellulose ether derivative, a cyclopolymer, a cationic polysaccharide, or a mixture thereof.

30. A composition according to claim 29, wherein said cyclopolymer is a dimethyldiallylammonium chloride homopolymer or a copolymer of dimethyldiallylammonium chloride and of acrylamide.

31. A composition according to claim 29, wherein said quaternary cellulose ether derivative is a hydroxyethylcellulose which has reacted with an epoxide substituted with a trimethylammonium group.

32. A composition according to claim 29, wherein said cationic polysaccharide is a guar gum modified with a 2,3-epoxypropyltrimethylammonium salt.

33. A composition according to claim 27, wherein said amphoteric polymer is a copolymer of dialkyldiallylammonium and of acrylic or methacrylic acid and/or a chitosan partially modified with a dicarboxylic acid.

34. A composition according to claim 1, comprising various cosmetically acceptable adjuvants selected from a fragrance, a preserving agent, a sequestering agent, a foam synergist, a foam stabilizer and an acidifying or a basifying agent.

35. A shampoo comprising the composition as defined in claim 1.

36. A shower gel comprising the composition as defined in claim 1.

37. A method for washing and/or conditioning keratin substances, said method comprising applying to said keratin substances an effective amount of the foaming composition as defined in claim 1.

38. A method according to claim 37, wherein said method further comprises wetting said keratin substances before the application of said foaming composition.

39. A method according to claim 37, wherein said method further comprises rinsing said keratin substances following the application of said foaming composition.

40. A method according to claim 39, wherein said method further comprises allowing said composition to remain on said keratin substances after said application and before said rinsing.

41. A composition according to claim 1, wherein said keratin substances are the hair or the skin.

* * * * *